United States Patent [19]

Tsai et al.

[11] Patent Number: 5,258,477

[45] Date of Patent: Nov. 2, 1993

[54] MONOMERS AND POLYMERS CONTAINING ACETAL AND ALDEHYDE GROUPS

[75] Inventors: John J. Tsai, Belle Mead; Patrick G. Jobe, Westfield; Robert L. Billmers, Stockton; Rama S. Chandran, South Bound Brook; Paul R. Mudge, Belle Mead; Michael T. Sarkis, Lawrenceville, all of N.J.

[73] Assignee: National Starch and Chemical Investment Holding Corporation, Bridgewater, N.J.

[21] Appl. No.: 598,565

[22] Filed: Oct. 16, 1990

Related U.S. Application Data

[63] Continuation of Ser. No. 411,440, Sep. 22, 1989, abandoned.

[51] Int. Cl.$^5$ .................. C08F 16/34; C07D 319/06; C07C 69/34; C07C 213/00
[52] U.S. Cl. .................... 526/315; 526/266; 526/270; 526/304; 526/307.5; 549/375; 549/454; 549/501; 549/502; 549/483; 549/495; 560/198; 560/222; 560/224; 564/292
[58] Field of Search ........... 526/315, 266, 270, 304, 526/307.5; 549/375, 454, 501, 502, 483, 495; 560/198, 222, 224; 564/292

[56] References Cited

U.S. PATENT DOCUMENTS

| | | | |
|---|---|---|---|
| 2,417,404 | 3/1947 | Minsk et al. | 269/34 |
| 2,485,239 | 10/1949 | Izard | 260/67 |
| 3,271,377 | 9/1966 | Mantell et al. | 526/266 |
| 4,191,838 | 3/1980 | Merger et al. | 560/205 |
| 4,250,070 | 2/1981 | Ley et al. | 260/29.6 |
| 4,281,207 | 7/1981 | Wilson | 568/433 |
| 4,508,579 | 4/1985 | Jansma et al. | 162/135 |
| 4,605,718 | 8/1986 | Jansma et al. | 526/240 |
| 4,610,920 | 9/1986 | Mudge et al. | 428/288 |
| 4,663,410 | 5/1987 | Pinschmidt, Jr. et al. | 526/263 |
| 4,866,151 | 9/1989 | Tsai | 527/300 |

FOREIGN PATENT DOCUMENTS 0364798  4/1990  European Pat. Off. .

OTHER PUBLICATIONS

Abstract from World Patents Index of West German Offenlegunschrift No. DE-OS 2,757,206.
Abstract from World Patents Index of U.S. Pat. No. 4,605,781.

*Primary Examiner*—Paul R. Michl
*Assistant Examiner*—P. Niland
*Attorney, Agent, or Firm*—Margaret B. Kelley; Edwin M. Szala

[57] ABSTRACT

Various novel acetal- and aldehyde-containing monomers are prepared. They can be polymerized and copolymerized by conventional polymerization techniques. The polymers contain repeating units derived from one or more ethylenically or allylically unsaturated monomers containing an acetal group or aldehyde group and optionally one or more repeating units derived from ethylenically or allylically unsaturated monomers other than the acetal-containing or aldehyde-containing monomer such as ethylene, vinyl acetate, ethyl acrylate, butyl acrylate, 2-ethylhexyl acrylate, hydroxyethyl acrylate, hydroxypropyl acrylate, methyl methacrylate or acrylic acid. Aqueous emulsions of polymers containing the acetal-containing monomers and a hydroxy-containing monomer are useful as binders for nonwoven fabrics.

10 Claims, No Drawings

MONOMERS AND POLYMERS CONTAINING ACETAL AND ALDEHYDE GROUPS

This is a continuation of co-pending application Ser. No. 411,440, filed on Sep. 22, 1989, now abandoned.

BACKGROUND OF THE INVENTION

This invention relates to novel acetal-containing and aldehyde-containing monomers capable of homopolymerization and/or copolymerization with other monomers to give polymers containing acetal and/or aldehyde groups. It also relates to the preparation of the aldehyde-containing polymers from the corresponding acetal-containing polymers. It further relates to the use of the polymers as crosslinkable coatings, adhesives, and nonwoven binders.

Blocked aldehydes of unsaturated compounds have been described in various patents. Most of these relate to dialkyl acetals and diacetates of aliphatic aldehydes.

U.S. Pat. No. 2,417,404 (issued Mar. 11, 1947 to L. M. Minsk et al.) and U.S. Pat. No. 2,485,239 (issued Oct. 18, 1949 to E. F. Izard) describe the preparation and copolymerization of diacetates of olefinic aldehydes.

U.S. Pat. No. 4,191,838 (issued Mar. 4, 1980 to F. Merger et al.) describes acrylate and methacrylate esters of 2,2-dimethyl-3-hydroxy-propanaldehyde and U.S. Pat. No. 4,250,070 (issued Feb. 10, 1981 to G. Ley et al.) describe polymers prepared from these aldehyde-containing monomers. The polymers are cured (i.e., crosslinked) with hydrazine-containing derivatives which are known to be toxic.

U.S. Pat. No. 4,663,410 (issued May 5, 1987 to R. K. Pinschmidt, Jr. et al.) describes blocked aldehyde monomers from aliphatic amino-aldehydes.

U.S. Pat. No. 4,281,207 (issued Jul. 28, 1981 to J. C. Wilson) and U.S. Pat. No. 4,225,689 (issued Sep. 30, 1980 to J. C. Wilson et al.) describe vinyl aryl ethers of aromatic phenolic aldehydes. The aryl vinyl ethers are derived from vinyl benzyl chloride and a phenolic aldehyde which is not masked or blocked. This is known to cause problems during polymerization and copolymerization.

There is a need for crosslinkable acetal-containing polymers and for aldehyde-containing polymers wherein the method for introducing the aldehyde groups is not dependent on reaction with an aldehyde-containing monomer.

SUMMARY OF THE INVENTION

The present invention provides novel acrylate, methacrylate, acrylamide, and methacrylamide, and diallylammonium halides monomers which contain aliphatic acetal or aldehyde groups. It also provides particularly interesting monomers which are prepared by the esterification of 2,2-dimethyl-3-hydroxy-propanaldehyde with $\alpha,\beta$-unsaturated acids such as crotonic, maleic, fumaric, or itaconic acid. The monomers have the general structure

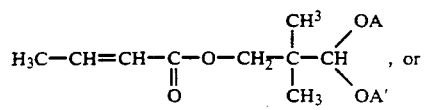

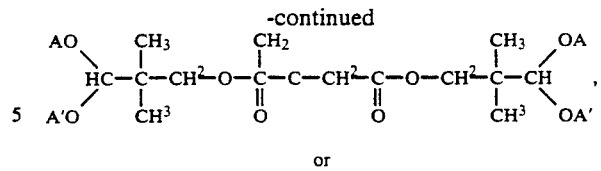

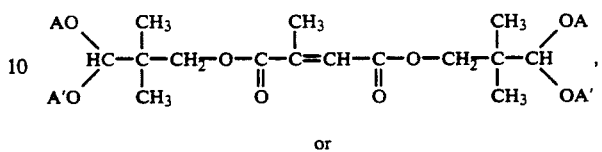

where A and A' are independently a lower alkyl or A and A' together form at least a 5-membered cyclic acetal. The starting materials are inexpensive and commercially available and the monomers are easier to prepare, store, and handle than monomers prepared using esters of acrylic or methacrylic acid. The latter are known to have a great propencity to premature homopolymerization and crosslinking during their preparation. The resulting aldehyde-containing monomers are converted to the acetals by reaction with an alcohol.

The present invention also provides novel monomers which contain aromatic acetal or aldhyde groups and which have the general structure

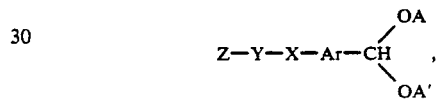

or Z—Y—X—Ar—CHO, where Z is a polymerizable group A—Ar is $CH_2$—Ar when Y is O, N, or NH, or

or X—Ar is $CH_2$—$CH_2$—O—Ar or $CH_2$—CH(OH)—$CH_2$—O—Ar when Y is O Ar is a substituted or unsubstituted divalent aryl group, and A and A' are as defined above. The term aryl is intended to include not only conjugated hydrocarbons but also conjugated heterocyclic systems. They include monomers based on furfuraldehyde, benzene, or naphathalene which contain aromatic acetal or aldehyde groups.

The acetal-containing acrylate monomers include 2-(5,5-dimethyl-1,3-dioxan-2-yl)ethyoxyethyl acrylate, 2-(5,5-dimethyl-1,3-dioxan-2-yl)ethyl acrylate, and 1-(5,5-dimethyl-1,3-dioxan-2-yl)propyl acrylate. The acetal-containing methacrylate monomers include 2[2-(1,3-dioxolan-2-yl)-ethoxy]ethyl methacrylate, 2[2-(1,3-dioxolan-2-yl)-1-methylethoxy]ethyl methacrylate, and 3-[N-methyl, N-(2,2-dimethoxyethyl)amino-2-hydroxypropyl methacrylate. The acetal-containing acrylamide and methacrylamide monomers include N-[2-(5,5-dimethyl-1,3-dioxan-2-yl)ethyl acrylamide and N,N-dimethyl, N-[3-dioxolan-2-yl) ethoxyethoxy-2-hydroxypropyl methacrylamidopropylammonium chloride. The acetal-containing N-N-diallylammonium halide monomer is N-methyl, N-(2,2-dimethoxy)ethyl, N,N-diallylammonium bromide.

Particularly interesting monomers are based on the esters of $\alpha,\beta$-unsaturated acids. They include (3,3-dimethoxy-2,2-dimethyl) propyl crotonate, (3,3-dimethoxy-2,2-dimethyl) propyl fumarate, (3,3 dimethoxy-2,2- dimethyl) propyl maleate, (3,3-dimethoxy-2,2-dimethyl) propyl itaconate, bis(3,3-dimethoxy-2,2-dimethyl) propyl fumarate, bis(3,3-dimethoxy-2,2-dimethyl) propyl maleate, and bis(3,3-dimethoxy-2,2-dimethyl) propyl itaconate.

The novel monomers which contain aromatic acetal or aldehyde groups and which have the general structure

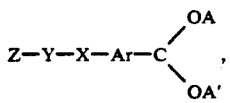

or Z—Y—X—Ar—CHO contain furan, benzene, naphthalene or similar aromatic groups.

The novel monomers based on furan acetal groups and have the general structure

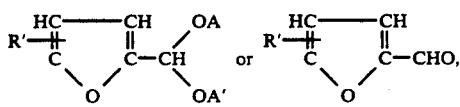

wherein R' is an ethylenically unsaturated group and A and A. are independently a lower alkyl or A and A' together form at least a 5-membered cyclic acetal.

Typical of the acetal-containing monomers are [5-(dimethoxymethyl)-furfur-2-yl)methyl acrylate and 5-(N,N-di[propyl-1-en-3-]aminomethyl)-2-dimethoxymethyl furan.

Typical of the aldehyde-containing monomers based on furan is 5-(N,N-di[propyl-1-en-3-]aminoethyl)-2-furancarboxyaldehyde.

Typical of the acetal-containing monomers based on benzene are phenyl (4-dimethoxymethyl)acrylate, phenyl (2-dimethoxymethyl)acrylate, 2-(2-(dimethoxymethylphenoxy)ethyl acrylate, 2-(2-[2-(1,3-dioxolano)]phenoxy)ethyl acrylate, 2-hydroxy-3-(4-dimethoxymethylphenoxy)propyl methacrylate, and 4-dimethoxymethyl)naphthyl methacrylate.

The present invention provides acetal-containing homopolymers and copolymers. The monomer repeating unit in the homopolymer is derived from one or more of the above ethylenically or allylically unsaturated monomers containing an acetal group

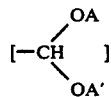

other than the acetal-containing monomers based on the esters of the α,β-unsaturated acids. The monomer repeating units in the copolymer are derived from one or more ethylenically or allylically unsaturated monomers containing an acetal group and from one or more ethylenically or allylically unsaturated monomers other than the acetal-containing monomer.

The acetal-containing monomers copolymerize very cleanly producing high molecular weight polymers with minimum precrosslinking. The polymers which contain acetal groups (often referred to as a blocked aldehyde groups) can be cured by self-crosslinking or through a hydroxyl-or amine-functionality introduced as a comonomer, coreactant, or reactive group present on the substrate to which the polymer is applied.

The present invention also provides aldehyde-containing homopolymers or copolymers. Polymerization of the aldehyde-containing monomers leads to low molecular weight polymers. The polymers may be crosslinked as described above. In the homopolymer the monomer repeating unit is derived from one or more ethylenically or allylically unsaturated monomers containing an aldehyde group (—CHO). In the copolymer the repeating units are derived from one or more ethylenically or allylically unsaturated monomers containing an aldehyde group and one or more ethylenically or allylically unsaturated monomers other than an aldehyde-containing monomer.

The practitioner will recognize that the monomer units may be randomly arranged or arranged alternately or in blocks and will vary depending upon the polymerization conditions and monomer reactivity. As used hereafter, the term "polymers" is intended to include homopolymers and copolymers.

The aldehyde-containing polymers may be prepared by hydrolyzing the acetal groups in an acetal-containing polymer. The hydrolysis is carried out at a pH of less than 7, preferably 5 or less, most preferably 2–4. The polymer can also be prepared by polymerizing an aldehyde-containing monomer. Direct polymerization, however, is not recommended.

The polymers containing the aliphatic acetals are useful, for example, as crosslinkable coatings, adhesives, and nonwoven binders. Vinyl polymer coatings can be crosslinked by mild acid catalysis to provide water - and solvent-resistant coatings. The acetal-containing polymers can be hydrolyzed to aldehyde-containing polymers and reacted with monomeric dye intermediates containing aldehyde reactive groups to form polymeric dye intermediates useful in color photography. The polymers based on the furfuraldehyde monomers are particularly useful when used in combination with crosslinking agents such as polyamines. The aldehyde-containing polymers are useful in the preparation of silver halide dispersions which have photographic applications.

DESCRIPTION OF THE PREFERRED EMBODIMENTS

The acrylate, methacrylate, acrylamide, and methacrylamide monomers of this invention can be prepared by reaction of acryloyl or methacryloyl chloride with amine-containing acetals.

The acetal-containing monomers may be prepared in three or more ways. The first type of reaction is that between an alcohol- or amino-containing acetal and an acryl or methacryl compound having a reactive site such as an acryl halide (e.g., acryloyl chloride), an epoxide (e.g., glycidyl methacrylate), or an isocyanate (e.g., isocyanatoethyl methacrylate). The second type of reactions is that between an alcohol- or amino-containing vinyl monomer and an acetal having a reactive site such as a chlorohydrin or an epoxide group (e.g., 2-(glycidyloxyethoxy)ethyl 1,3-dioxolane). The third type of reactions is that between two moles of an allyl halide and an amino-containing acetal or between diallylamine and an acetal with a reactive site such as those above. Styrene derivatives having a benzylic halide can also be used in preparing acetal-containing monomers. The acetal-containing monomers can be converted to aldehyde-containing monomers by treatment with acid at pH of 6 or less.

In addition to the above methods, a method involving direct esterification of the corresponding hydroxy-aldehyde with the α,β-unsaturated acids (e.g., crotonic, maleic, fumaric, and itaconic) using a strong mineral acid such as methane sulfonic, sulfuric, hydrochloric, or Lewis acids such as boron trifluoride, zinc chloride and the like can be used.

Both the acetal-containing or aldehyde-containing monomers are useful as polymerizable monomers. They may be used to form homopolymers or their mixtures may be used to form polymers thereof. They may also be used to form addition polymers with other ethylenically unsaturated monomers. The polymers may be prepared by solution, emulsion, precipitation, suspension, or bulk polymerization techniques. The preferred method is emulsion polymerization using a free radical and conventional emulsion techniques.

The first method involves the reaction of an alcohol-containing aromatic aldehyde or acetal (e.g., 5-hydroxymethyl-2-furfuraldehyde) with a polymerizable acid chloride (e.g., acryloyl chloride). The hydrogen chloride evolved in the reaction can be scavenged by a non-nucleophilic base (e.g., 2,4,6-collidine). This reaction can also be run in a two phase system in which the aqueous phase contains sodium hydroxide and the organic phase is a non-water miscible solvent (e.g., toluene). The resulting esters are isolated and purified by distillation. The second method involves the reaction of an aromatic chloromethyl aldehyde (e.g., 5-chloromethyl furfuraldehyde) with a polymerizable amine (e.g., vinyl amine) or polymerizable alcohol (e.g., allyl alcohol). The reaction is carried out in a non-reactive solvent (e.g., toluene, tetrahydrofuran, and the like). The reaction mixture is generally refluxed overnight. Acid scavengers may be used, but are not necessary. The products may be purified by distillation before use.

All of the above named monomers are also suitable for graft polymerization to polysaccharide substrates. The graft polymerization is described in U.S. Pat. No. 4,866,151 issued Sep. 12, 1989 to J. J. Tsai et al., the disclosure of which is incorporated herein by reference.

The polymers may be prepared using only the acetal-containing monomers. However, in some applications where the presence of fewer aldehyde groups is desirable, other typical comonomers can be used. These can include ethylenically unsaturated monomers which may contain anionic or cationic charges.

Suitable monomers include ethylene; styrene and substituted styrenes such as vinyl toluene, α-methyl styrene, chloromethylstyrene, and the like; compounds such as acrylic and methacrylic acids, or their salts, or their esters such as methyl, ethyl, butyl, 2-ethylhexyl acrylates and methacrylates; acrylamides and methacrylamides and their N-substituted derivatives; itaconic acid and its functional derivatives, preferably the esters; maleic anhydride; maleic and fumaric acids and their esters; acrylonitrile and methacrylonitrile; vinyl chloride; vinyl alkanoates, such as vinyl acetate, vinyl propionate, vinyl neodecanoate, vinyl pivalate, and the like; vinyl ethers; vinyl pyridine and vinyl pyrrolidone; vinyl ketones; vinylidene compounds, such as vinylidene chloride; allylidene compounds such as allylidene diacetates; conjugated diene monomers such as butadiene-1,3, isoprene, and chlorobutadiene-1,3; diallylamine and its respective salts; diallyl dialkyl quaternary ammonium salts; N,N-dialkylaminoalkyl acrylate and methacrylate and their respective salts, N,N-dialkylaminoalkyl acrylamide and methacrylamide and their respective salts; vinylbenzyldialkyl amine and their respective salts; acids such as vinylsulfonic acid, styrene sulfonic acid, (meth)acrylamidopropanesulfonic acid and their respective salts; and the like.

Acrylic or vinyl acrylic polymers useful for preparing crosslinkable compositions contain about 0.5 to 90%, preferably about 5 to 30%, of the acetal-containing monomer, about 0.5 to 90%, preferably about 5 to 30%, of a hydroxy-containing monomer, and about 9.5 to 99%, preferably about 40 to 90% of other acrylic or vinyl acrylic monomers. Ethylene vinyl ester polymers useful for preparing crosslinkable compositions contain about 0.5 to 90%, preferably about 1 to 20%, of the acetal-containing monomer, about 0.5 to 90%, preferably about 1 to 20%, of the hydroxy-containing monomer, about 5 to 35% ethylene, and about 65 to 95% vinyl ester. Suitable hydroxy-containing monomers include 2-hydroxyethyl acrylate or methacrylate, 2-hydroxypropyl acrylate or methacrylate, or vinyl alcohol (from the hydrolysis of vinyl acetate). Other suitable comonomers are discussed above. Particularly preferred are methyl, ethyl, butyl, and/or 2-ethylhexyl acrylates or methacrylates; vinyl acetate, vinyl propionate, vinyl neodecanoate, and/or vinyl pivalate; ethylene; styrene; acrylonitrile and/or methacrylonitrile; and acrylamide and/or methacrylamide.

The acetal-containing copolymers based on the esters of α,β-unsaturated acids are particularly useful as binders for nonwovens. The corresponding aldehyde-containing polymers are not preferred for this end use. Suitable nonwovens include pulp, rayon, and polyester nonwovens.

The starting fibrous web can be formed by any one of the conventional techniques for depositing or arranging fibers in a web or layer. These techniques include carding, garnetting, air-laying, and the like. Individual webs or thin layers formed by one or more of these techniques can also be lapped or laminated to provide a thicker layer for conversion into a heavier fabric. In general, the fibers extend in a plurality of diverse directions in general alignment with the major plane of the fabric, overlapping, intersecting and supporting one another to form an open, porous structure. When reference is made to "cellulose" fibers, those fibers containing predominately $C_6H_{10}O_5$ groupings are meant. Thus, examples of the fibers to be used in the starting web are the natural cellulose fibers such as wood pulp and chemically modified celluloses such as regenerated cellulose. Often the fibrous starting web contains at least 50% cellulose fibers, whether they be natural or synthetic or a combination thereof. Other fibers in the starting web may comprise natural fibers such as wool; artificial fibers such as cellulose acetate; synthetic fibers such as polyamides (e.g., nylon), polyesters (e.g., "Dynel", "Acrylan", "Orlon"), "Orlon,"), polyolefins such as polyethylene, polyvinyl chloride, polyurethane, and the like, alone or in combination with one another.

The fibrous starting layer or web suitably weighs from about 5 to 65 grams per square yard and generally weighs about 10 to 40 grams per square yard. This fibrous starting layer, regardless of its method of preparation, is then subjected to at least one of the several types of latex bonding operations to anchor the individual fibers together to form a self-sustaining web. Some of the better-known methods of bonding are overall impregnation, spraying or printing the web with intermittent or continuous straight or wavy lines or areas of binder extending generally transversely or diagonally across the web and, additionally if desired, along the web.

The amount of binder, calculated on a dry basis, applied to the fibrous starting web suitably ranges from about 10 to about 100 parts or more per 100 parts of the starting web, and preferably from about 20 to about 45 per 100 parts of the starting web. The impregnated web is then dried and cured. The fabrics are suitably dried by passing them through an air oven or over a series of heated cans or the like and then through a curing oven or sections of hot cans. Ordinarily, convection air drying is effected at 65°–95° C. for 2–6 minutes, followed by curing at 145°–155° C. for 1–5 minutes or more. However, other time-temperature relationships can be employed, as is well known in the art, shorter times at higher temperatures or longer times at lower temperatures being used. For example, the curing step can be carried out at about 135° C. for about 15 minutes or more in a laboratory or pilot line but may require only 2 to 20 seconds on high pressure, high efficiency steam cans used in high speed production. If desired, the drying and curing can be effected in a single exposure or step.

Nonwoven fabrics prepared in accordance with this invention have greater strength than other resin bonded nonwovens of comparable softness levels and, as such, are competitive with woven fabrics and thermally bonded polyolefins.

It can be appreciated by the practitioner that a large number of variations may be effected in preparing selecting the monomers and comonomers and polymerizing them in accordance with the procedure described above without materially departing from the scope and spirit of the invention. Such variations will be evident to those skilled in the art and are to be included within the scope of the invention.

In the examples which follow, all parts and percentages are given by weight and all temperatures are in degrees Celsius unless otherwise noted.

The chemical structure of the monomers were verified by infrared, NMR, and/or GC-mass spectral analyses.

EXAMPLE I

This example describes the preparation of novel acetal-containing acrylate and methacrylate monomers.

2-(5,5-Dimethyl-1,3-dioxan-2-yl)ethoxyethyl acrylate

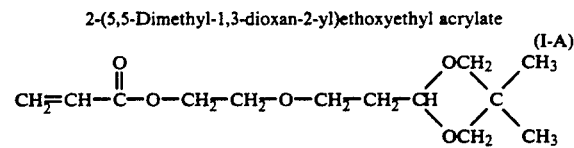

(I-A)

A mixture of hydroxyethyl acrylate (11.6 g.), an equivalent amount of 2-ethylenyl-5,5-dimethyl-1,3-dioxane (EDD) (14.2 g.), and a catalytic amount of p-toluenesulfonic acid (100 mg.) was heated at 65° C. overnight. Gas chromatography showed the reaction occurred. The unreacted starting materials were removed at 40° C. under 0.05 mm Hg.

2-(5,5-Dimethyl-1,3-dioxan-2-yl)ethyl acrylate

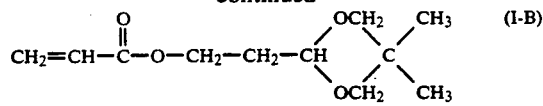

(I-B)

In the presence of a catalytic amount of p-toluenesulfonic acid (100 mg.) a mixture of acrylic acid (7.20 g., 0.1 mole) and 2-ethylenyl-5,5-dimethyl-1,3-dioxane (14.2 g.) was stirred at 60° C. for 16 hours. Gas chromatography separation (the column temperature was raised from 50° C. to 200° C. at a rate of 15° C./minute) showed a major product at 8.40 minutes and some unreacted unsaturated acetal at 1.50 minutes. Both unreacted starting materials were easily stripped off under vacuum.

[1-(5,5-Dimethyl-1,3-dioxan-2-yl]-2-propyl acrylate

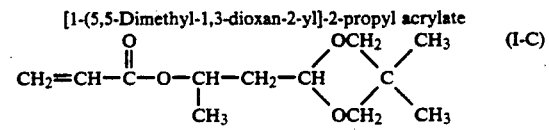

(I-C)

2-Propenyl-5,5-dimethyl-1,3-dioxane (PDD) was reacted with acrylic acid under the same conditions as the reaction with EDD (see Monomer I-B).

2[2-(1,3-Dioxolan-2-yl)-ethoxylethyl methacrylate

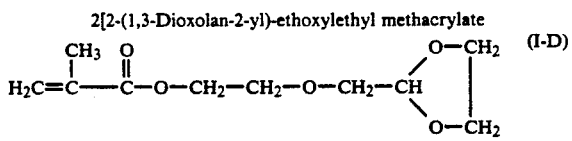

(I-D)

To a 500 ml. four-neck round bottom flask equipped with a mechanical stirrer, condenser, thermometer and addition funnel were added initially 22.0 g. triethylamine, 32.4 g. 2-[2(2-hydroxyethoxy)-ethyl]-1,3-dioxolane, and 100 ml. methylene chloride and then 23.22 g. methacryloyl chloride were added dropwise. The temperature was reduced to about 0° C. to −5° C. A total of 24.6 g. methacryloyl chloride was added dropwise through an addition funnel. While maintaining the temperature at about 0° to −5° C., the mixture was then allowed to warm to room temperature and stirred for 30 min. and added to a equal volume (180 ml.) of ice-water. The methylene chloride layer was separated from the aqueous layer, a small mount of anhydrous magnesium sulfate (3 g.) was added, the solution was filtered, and methylene chloride was stripped off to isolate the product. Purification was done by as above at 65.2° C. under 0.5 mm. Hg pressure. The monomer was purified by distillation at 106° C. under 0.2 mm Hg pressure.

2[2-(1,3-Dioxolan-2-yl)-1-methylethoxyethyl methacrylate

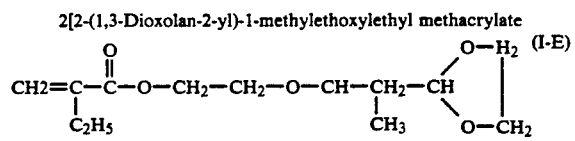

(I-E)

Following the above procedure, the monomer was prepared using 22 g. triethylamine, 35.2 g. 2-[2-hydroxyethoxy)propyl]-1,3-dioxolane, 23.22 g. methacryloyl chloride, and 180 ml. methylene chloride. The product was purified by vacuum distillation at 93.2° C. under 0.2 mm. Hg pressure.

3-(N-Methyl, N-2,2-dimethoxyethyl)amino-2-hydroxypropyl methacrylate (I-F)

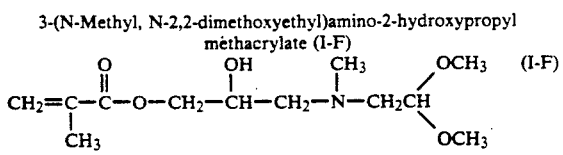

Glycidyl methacrylate (14.2 g.) was reacted with 11.9 of methylaminoacetaldehyde dimethyl acetal at 75° C. for 3 hours in the presence of a catalytic amount of tetrabutyl-ammonium chloride (150 mg.) and a inhibitor (50 mg. of 4-t-butyl cathechol). Air was passed through the reaction mixture to prevent polymerization reactions. The product was isolated by vacuum distillation at 118° C. under 0.05 mm Hg pressure.

EXAMPLE II

This example describes the preparation of novel acetal-containing acrylamide and methacrylamide monomers.

N-[2-(5,5-Dimethyl-1,3-dioxan-2-yl)ethyl acrylamide

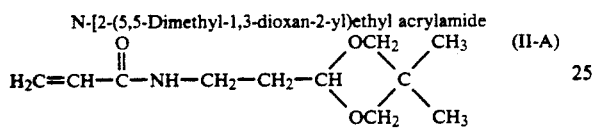

The product was prepared by reacting the unsaturated acetal (EDD) with acrylamide using a procedure similar to that described for monomers I-D.

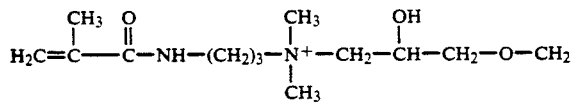

Dimethylaminopropyl methacrylamide (DMAPMA) was reacted with 2-(glycidyloxyethoxy)ethyl 1,3-dioxolane under acidic conditions to give the monomer. Thin-layer chromatograph separation showed Rf 0.58, 0.35, and 0.18 for DMAPMA, 2-(glycidyloxyethoxy)ethyl 1,3-dioxolane, and the monomer, respectively (eluant: 50/50 toluene-methanol). The monomer can be purified by column chromatography.

EXAMPLE III

This example describes the preparation of a N, N-diallyl-ammonium chloride monomer containing acetal groups.

N-Methyl, N-(2,2-dimethoxy)ethyl, N,N-diallylmmonium bromide

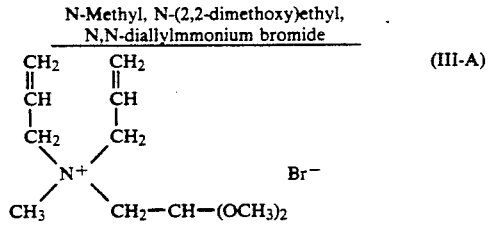

To a 250 ml. four-neck round bottom flask, equipped as described in Example I, were added 23.83 g. N-methylacetaldehyde dimethyl acetal and 25 ml. tetrahydrofuran. Then 24.18 g. allyl bromide were added slowly. While maintaining the temperature at about 0° C. After the addition was completed, the temperature was brought to 40° C. and the reaction mixture was stirred for 6 hours. It was then cooled in 0° C. and 50% aqueous sodium hydroxide solution (16 g) was added. Then, another equivalent amount of allyl bromide (24.18 g) was added slowly. The temperature was raised to 50° C. and the reaction mixture was stirred overnight. The reaction mixture was concentrated on a rotary evaporator. Acetone (400 ml) was added to the viscous liquid to precipite the inorganic salt which removed by filtration. The acetone solution was concentrated on the rotary evaporator to give the final product. The moisture of this ammonium salt could not be determined accurately. The ionic bromide was 26.78% (expected 28.52%) and the organic bromide was 0%.

EXAMPLE IV

This example describes the preparation of novel acetal- and aldehyde-containing monomers based on crotonic and maleic acid.

(3,3-Dimethoxy-2,2-dimethyl)propyl crotonate (DMDPC)

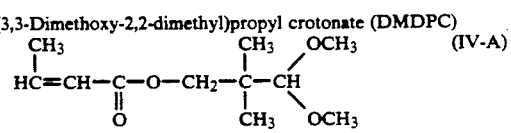

This monomer was prepared in two steps. In the first step, 2, 2-dimethyl-3-hydroxy propanaldehyde was esterified with crotonic acid in the presence of a strong acid. In the second step the intermediate ethyl (2,2-dimethyl-2-formyl)crotonate (EDFC) was converted to the monomer by reaction with methanol and trimethyl

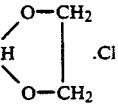

orthoformate.

In a 2 l. reaction flask fitted with a mechanical stirrer, thermometer, Dean-Stark water trap, condenser and a heating mantle were placed crotonic acid (258 g. 3 mole), 2,2-dimethyl-3-hydroxy propanaldehyde (204 g., 2 mole), toluene (500 g.), 70% methanesulfonic acid (41 g., 0.3 mole), and cupric chloride (0.050 g., 0.36 mmol). The reaction mixture was heated to 60° C. for 2 hours to reflux when the water from the reaction was azeotroped into the trap. The reaction was continued until no more water could be azeotroped. A total of 47 g. of water was collected in 5 hours, indicating that the reaction was essentially complete. The reaction mixture was cooled, and the excess acid was neutralized with aqueous sodium hydroxide and washed with water until the washings were neutral. The toluene solution containing the product was dried over anhydrous magnesium sulfate and filtered. Toluene was removed under reduced pressure and the residue was vacuum distilled (58°–65° C., 0.1 mm Hg) to obtain 142 g. of pure ethyl(2,2-dimethyl-2-formyl) crotonate.

The intermediate ethyl (2,2-dimethyl-2-formyl) crotonate was converted to the dimethyl acetal. To a 1 l. reaction flask fitted with a mechanical stirrer, thermometer, reflux condenser, CaCl$_2$ moisture guard tube and a heating mantle were placed ethyl (2,2-dimethyl-2-formyl) crotonate (85 g., 0.5 mole), absolute methanol (150 g.), trimethyl orthoformate (53 g., 0.5 mole) and crosslinked poly(styrenesulfonic acid) catalyst (2 g.). The reaction mixture was refluxed for 1 hour. When the reaction was completed, as monitored by H-1 NMR spectroscopy for the disappearance of the aldehyde and appearance of the acetal peaks, the reaction mixture was cooled and the catalyst was filtered off. The solvent, methanol, and volatile components were removed under reduced pressure to obtain 103 g. of pure (3,3-dimethoxy-2,2-dimethyl)propyl crotonate.

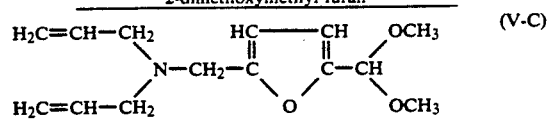

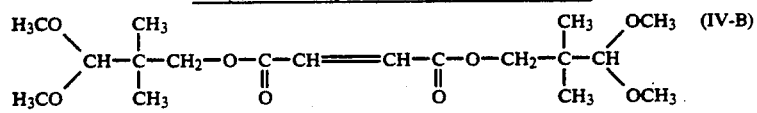

The monomer was prepared according to the procedure described above except that maleic anhydride was used in place of crotonic acid in the first step and the mole ratio of maleic anhydride to 2,2-dimethyl-3-hydroxy propanaldehyde was 1:2 and of the intermediate aldehyde to trimethyl orthoformate was also 1:2 in the second step of this reaction.

EXAMPLE V

Part A

This example describes the preparation of novel aldehyde-containing and acetal-containing aromatic monomers.

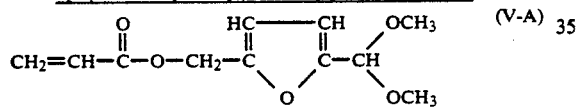

To a 500 ml. four-neck round bottom flask equipped with a mechanical stirrer, condenser, thermometer, and addition funnel were added triethylamine (10.3 g.), 2-hydroxymethyl furfural dimethyl acetal (17.2 g.), and methylene chloride (90 ml.). The temperature was brought down to 0°-5° C., and acryloyl chloride (9.23 g.) was added dropwise through an addition funnel while the temperature was maintained at between 0° C. and −5° C. After the addition was completed, the bath was warmed to room temperature and stirred for 30 min. The reaction mixture was added to an equal volume (90 ml.) of ice-water. The methylene chloride layer was separated from the aqueous layer in a separatory funnel. A small amount of anhydrous magnesium sulfate was added to the methylene chloride solution. The methylene chloride was filtered and stripped to isolate the product which was purified by vacuum distillation at 95° C. under 0.5 mm Hg pressure.

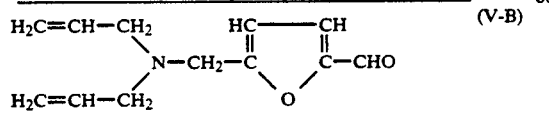

Using the procedure described above chloromethyl furfuraldehyde and diallylamine were reacted to provide the above monomer.

The above-acetal containing monomer was prepared by treating the monomer designated V-B with methanol in the presence of a trace amount of p-toluene sulfonic acid.

Part B

The following aromatic aldehyde- or acetal-containing containing monomers can be prepared using the above procedure and indicated reagents.

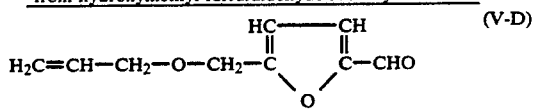

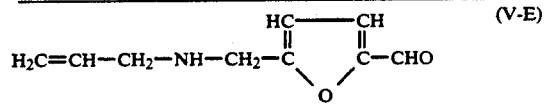

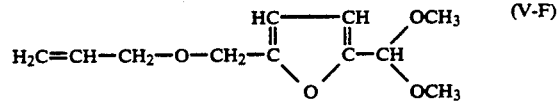

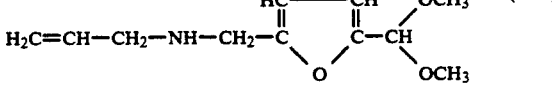

from chloromethyl furfuraldehyde and allyl amine, followed by treatment with methanol to convert the aldehyde to the acetal.

EXAMPLE VI

This example describes the preparation of monomers containing aromatic acetal groups.

Part A

Phenyl(4-dimethoxymethyl)acrylate (PDMA-4)

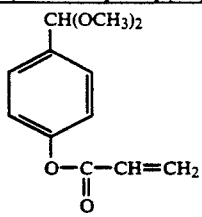
(VI-A)

The preparation was carried out in two steps. In the first step 122 g. (1 mole) 4-hydroxybenzaldehyde, 150 g. absolute methanol, 124 g. (1.2 mole) trimethyl orthoformate and 2.5 g. (0.017 mole) polyvinylpyridinium hydrochloride (PVP.HCl) (prepared from polyvinyl pyridine and sold under the trade name Reillex 425) were added to a 1 l. 4-neck flask equipped with a mechanical stirrer, condenser, calcium chloride drying tube and a thermometer. The mixture was heated under reflux (65° C.) for 1 hr. The solution was cooled and 2 g. (0.019 mole) anhydrous sodium carbonate were added. The mixture was stirred for 15 min. The insoluble inorganic salts and the PVP.HCl catalyst were filtered off under suction. The dimethoxymethyl phenol was isolated by removing the solvent and other volatile by-products under reduced pressure using a Rotovap. The residue was kept under a high vacuum (0.5 torr) for 1 hr. to remove any residual volatile components. The product was obtained as a light yellow oil. The yield was 98% (165 g.). The product was characterized by IR and H-1 NMR. The IR showed no aldehyde carbonyl band at 1685 cm$^{-1}$. The H-1 NMR showed signals for methoxy methyl at 3.3 ppm but no aldehyde proton at 10.4 ppm. The purity of the sample was determined to be 96% from its GC on a carbowax-20M column.

In the second step, 107.5 g. (1.1 moles) triethylamine, 168 g. (1 mole) dimethoxymethyl phenol from the 1st step, and 875 ml. anhydrous ether were placed in a 3 l. 4-neck flask equipped with mechanical stirrer, condenser, 250 ml. pressure equalized addition funnel and thermometer. The solution was cooled to 5° C. in an ice/salt mixture. A solution of 95 g. (1.05 mole) acryloyl chloride in anhydrous ether (125 ml.) was placed in the addition funnel. The acryloyl chloride solution was added at a rate sufficient to maintain the temperature below 10° C. The reaction mixture was stirred for an additional 30 min. after the acryloyl chloride addition was completed. The ice bath was removed and the reaction mixture was allowed to warm to room temperature. It was stirred for an additional 2 hr. after which the triethylamine hydrochloride was filtered off under suction. The filtrate was washed three times with 150 ml. of 0.1N sodium hydroxide, washed with water until neutral (pH 6-7), and then washed twice with 50 ml. of saturated sodium chloride. The ether layer was dried over anhydrous magnesium sulfate and filtered. The solvent was removed under reduced pressure. The crude product was distilled under high vacuum (110° C., 0.1 mm Hg) to obtain 195 g. (88% yield) of the monomer. The monomer was characterized by H-1 NMR and GC. H-1 NMR taken in CDCl$_3$ showed peaks at 5.8 and 6.5 ppm for the acrylate protons (3H) in addition to the signals for DMMP.

Phenyl(2-dimethoxymethyl)acrylate (PDMA-2)

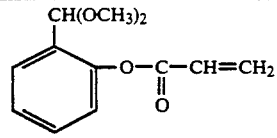
(VI-B)

The two step preparation was carried out as above using 2-hydroxybenzaldehyde instead of 4-hydroxybenzaldehyde.

2-(2-Dimethoxymethylphenoxy)ethyl acrylate (DMPEA-2)

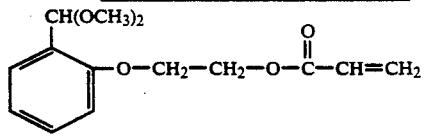
(VI-C)

The synthesis was carried out in 3 steps. In the first step 2-(2-hydroxyethoxy) benzaldehyde (2-HEBA) was prepared according to the procedure described by J. Almog, et al. in Tetrahedron, 1981, 37, 3589. In the second step 2-(2-hydroxyethoxy) benzaldehyde acrylic acid ester was prepared. In the third step the 2-(2-dimethoxymethylphenoxy) ethyl acrylate was prepared.

To a 1 l. round-bottomed flask fitted with a Dean-Stark tube, mechanical stirrer, thermometer, condenser, and a vented air inlet were placed 166 g. (1 mole) of the 2-(2-hydroxyethoxy) benzaldehyde from the first step, 216 g. (3 moles) acrylic acid, 800 ml. cyclohexane, 9.6 g. (0.1 mole) methane sulfonic acid and 4 g. (0.008 mole) 4-methoxyphenol. The reaction mixture was heated to reflux under a slow stream of air and the water azeotrope was separated at the Dean-Stark trap. The reaction was complete in 4 hr. at which time 19 ml. of aqueous distillate had been collected. By titration this distillate was found to contain 10% of acrylic acid.

The reaction mixture was cooled and cyclohexane was distilled off under reduced pressure (45° C., 160 mm.) followed by the acrylic acid (50-55° C., 15 mm.). The residue after distillation was dissolved in 600 ml. ether and washed with 1N sodium hydroxide until the aqueous washings were distinctly basic (pH 9 to 10) followed by washing with water until the washings were neutral. The organic layer was washed with 50 ml. of saturated sodium chloride and dried over anhydrous sodium sulfate (50 g.). The ether solution was filtered and the solvent removed under reduced pressure. The brown oily residue (178 g.) crystallized on standing. The yield was 81%. The ester was purified by crystallization from hot cyclohexane (75 ml. per g. of ester). The white needles had a melting point of 48°-50° C. H-1 NMR taken in CDCl$_3$ showed signals at ppms 4.4 (m, 4H), 5.8 (m, 1H), 6.3 (m, 2H), 6.9-7.6 (m, 4H) and 10.4 (s 1H).

The dimethyl acetal of the acrylic acid ester from step 2 was prepared using the procedure described in the first step for the preparation of phenyl (4-dimethoxymethyl) acrylate (VI-A). Typically, a reaction of 220 g. (1 mole) of the above acrylate gave 258 g. of a light yellow oil. The product can be further purified by short path (Kugel Rohr) vacuum distillation (110° C., 0.1 mm Hg). H-1 NMR in CDCl$_3$ shows signals at ppms 3.4 (s, 1H), 4.4 (m, 4H), 5.7 (s, 1H), 5.9 (m, 1H), 6.3 (m, 2H), 6.9-7.6 (m, 4H) and no signal at 10.4.

PDMA-2 and PDMA-4 can also be prepared by first making the 2- or 4-formyl phenoxy propenoate by reacting the respective hydroxybenzaldehydes with acryloyl chloride in the presence of an acid scavenger similar to step 2 of the PDMA-4 synthesis. The dimethyl acetal of the 2- or 4-formyl phenoxy acrylate was prepared using the same procedure described in step 1 of PDMA-4 synthesis.

2-(2-[2-(1,3-Dioxan-2-yl)]phenoxy)ethyl acrylate (DPEA-2)

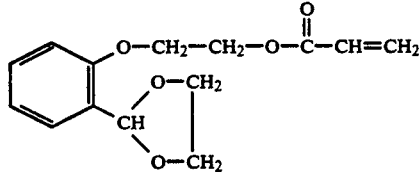

(VI-D)

It was prepared from 2-(2-hydroxyethoxy)benzaldehyde acrylic acid ester (see Step 2 of 2-DMPEA synthesis).

In a 500-ml. round-bottomed flask fitted with a Dean-Stark trap, condenser, mechanical stirrer, thermometer, and a heating mantle was placed 2-(2-formylphenoxy)ethyl acrylate (2-FPEA) (110 g., 0.5 mole), ethylene glycol (47 g., 0.75 mole), cyclohexane (250 ml.) polystyrene sulfonic acid (Dow M-31 resin) (5 g.), and 4-methoxyphenol (0.05 g.). The reaction mixture was refluxed for 3 hours. When 9 ml. of water was collected, the reaction was complete.

The reaction mixture was cooled and filtered through a wire mesh to remove the resin catalyst. The mixture had two phases. The upper phase containing cyclohexane was discarded. The lower phase was dissolved in ethyl ether (250 ml.). The ether solution was washed five times with water (100 ml.) to remove the unreacted glycol and then washed with a saturated sodium chloride solution. The ether solution was dried over anhydrous sodium sulfate and filtered. The solvent was removed under reduced pressure and then under high vacuum to obtain 120 g. (90% yield) of the monomer. By H-1 NMR analysis the product showed signals consistent with the structure shown above. The presence of 5 mol % of unreacted aldehyde indicated it was 97% pure.

2-Hydroxy-3-(4-dimethoxymethylphenoxy)propyl methacrylate

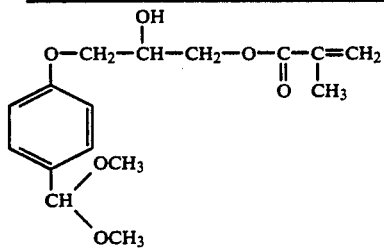

(VI-E)

In a 500 ml. 4-neck flask fitted with a mechanical stirrer, thermometer, condenser and a vented nitrogen bubbler were placed 84 g. (0.5 mol) 4-dimethoxymethyl phenol, 71 g. (0.5 mol) glycidyl methacrylate (GMA), and 1.5 g. (0.005 mol) benzyltributylammonium chloride. The apparatus was flushed with air for 5 minutes. The solution was heated to 80° for 5 hours. The progress of the reaction was followed by the disappearance of the GMA by GC analysis of the reaction mixture which indicated 95% reaction. The solution was cooled and dissolved in 250 ml. of methylene chloride and washed three times with 1N sodium hydroxide (100 ml.) followed by water until the washings were neutral. The organic layer was dried over magnesium sulfate and the solvent was removed at reduced pressure (Rotovap). The oily residue was dried under high vacuum for 30 min. to obtain 133 g. (86%) product of the monomer. H-1 NMR of the product showed signals typical to glycidyl methacrylate except that the signal for the protons that were attached to the epoxide carbon at 2.8 and 3.3 ppm showed up as doublets and a quintet respectively. The spectrum also showed signals for the 4-dimethoxymethyl phenyl group at ppms 7.8–6.9 and 3.4.

2-Hydroxy-3-(2-dimethoxymethylphenoxy)propyl methacrylate

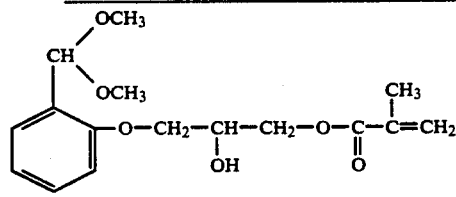

(VI-F)

The monomer was prepared by the procedure described above starting with the 2-dimethoxymethyl phenol instead of 4-dimethoxymethyl phenol.

EXAMPLE VII

This example demonstrates that the aldehyde-containing monomer designated V-A of Example V can be polymerized. Using standard emulsion polymerization techniques the monomer was polymerized with methyl methacrylate (MMA), ethyl acrylate (EA), and 2-hydroxyethyl acrylate (2-HEA). Sodium persulfate was used as initiator. The resulting latex had a solids content of 47.1%, Brookfield viscosity of 60 cps., and pH of 3.1. The polymer of EA/MMA/2-HEA/CHO-monomer (80.5/4.5/5.5/9.5) was cast as a film. After air-drying the % insolubles were 81.8%; after drying for 5 min. at 130° C. the % insolubles were 83.8%.

EXAMPLE VIII

Part A

Acrylic solution polymers containing monomer units derived from acetal-containing monomers were prepared. The polymer compositions indicated in Table I were prepared. The acetal-containing monomers used were those identified as PDMA-4 and PDMA-2 (monomers VI-A and VI-B) whose preparation is described in Example VI. A comparative polymer containing the crosslinkable monomer N-methylolacrylamide (NMA) was also prepared. The PDMA-4 monomer was used at a higher wt. % than the NMA monomer to maintain the same mole % of crosslinkable monomers. The polymerizations were carried out in ethyl alcohol using azoisobutyronitrile as the initiator. The solids were 38–40%.

Because the polymerization was carried out in alcohol the polymers obtained were both low molecular weight and had high branching due to chain transfer to solvent or the PDMA monomer. Alcohol was used since the NMA monomer used in the comparative polymer is insoluble in other hydrocarbons.

To determine the crosslinking ability of the polymers films were cast and cured. The cure was catalyzed with 1% ammonium chloride. Insolubles were determined in boiling tetrahydrofuran and filtration was carried out using a Millipore 0.45 micron filter.

The results show that the polymers containing the acetal-containing monomers were incorporated into the polymer and were capable of crosslinking through the acetal even at 5 weight % monomer.

15 minutes. After the 15 minute hold, the process was repeated with 0.5 g. sodium metabisulfite in 20 g. water. After this procedure the internal temperature was cooled to 25°–30° C. and the emulsion was discharged.

All acrylic and styrene/acrylic latex compositions, as well as the N-methylol acrylamide-containing comparative polymers, were prepared using the above procedure except for the necessary monomer modifications.

In the all acrylic latex recipe, 30 g. ethyl acrylate and

TABLE I

Polymerization and Crosslinking of Polymers Containing PDMA-4 and PDMA-2

| | A | | B | | C | | D | | E | | F | | G | | H* | |
|---|---|---|---|---|---|---|---|---|---|---|---|---|---|---|---|---|
| Monomer | Wt % | Mol % | Wt % | Mol % | Wt % | Mol % | Wt % | Mol % | Wt % | Mol % | Wt % | Mol % | Wt % | Mol % | Wt % | Mol % |
| EA | 71.2 | 78.3 | 78.3 | 84 | 79.4 | 8.23 | 82.0 | 85.0 | 79.4 | 82.4 | 82 | 85 | 85 | 82.4 | 77 | 78.5 |
| MA | — | — | — | — | — | — | — | — | — | — | — | — | — | — | — | — |
| MMA | 4.45 | 4.83 | 4.84 | 5.2 | 9.8 | 10.2 | 10.13 | 10.5 | 9.8 | 10.2 | 10.1 | 10.5 | 10.0 | 10.2 | 4.75 | 4.85 |
| HEA | 12.74 | 11.7 | 5.8 | 5.2 | 5.8 | 5.1 | 2.7 | 2.5 | — | — | — | — | — | — | 13.6 | 11.7 |
| HPA | — | — | — | — | — | — | — | — | 5.8 | 5.1 | 2.7 | 2.5 | 6.0 | 5.1 | — | — |
| PDMA-4 | 10.6 | 5.2 | 11.1 | 5.3 | 4.95 | 2.4 | 5.1 | 2.5 | — | — | — | — | — | — | — | — |
| PDMA-2 | — | — | — | — | — | — | — | — | 5.0 | 2.3 | 5.1 | 2.5 | 2.3 | 2.3 | — | — |
| NMA | — | — | — | — | — | — | — | — | — | — | — | — | — | — | 4.75 | 4.85 |
| % Insoluble. | 94 | | 85 | | 75 | | 77 | | 64 | | 75 | | 80 | | 88 | |

*Comparative
EA is ethyl acrylate
MA is methyl acrylate
MMA is methyl methacrylate
HEA is hydroxyethyl acrylate
HPA is hydroxypropyl acrylate
PDMA-4 is phenyl(4-dimethoxymethyl) acrylate
PDMA-2 is phenyl(2-dimethoxymethyl) acrylate
NMA is N-methylol acrylamide

EXAMPLE IX

This example describes the preparation of non-woven emulsion binders.

A 2 l. four-necked round bottom glass flask equipped with a heating/cooling means, variable rate stirrer and means of metering monomers and initiators was employed. To the flask were charged 1.0 g. dodecyl benzene sulfonate as a 20% w/w water solution, 3.0 g. Triton X305 (an alkyl aryl polyethylene oxide with 30 moles ethylene oxide) as a 70% w/w water solution, 0.5 g. ferrous sulfate solution as a 1% water solution, and 0.6 g. sodium acetate and 0.1 g. sodium metabisulfate in 420 g. of water. After purging with nitrogen, 50 g. vinyl acetate and 5 g. butyl acrylate were charged to the reactor. The contents were then heated to 50° C. The polymerization was initiated by simultaneously metering in solutions of 1.5 g. t-butylhydroperoxide and 0.15 g. ammonium hydroxide in 40 g. water and 1.7 g. sodium metabisulfite and 0.15 g. ammonium hydroperoxide in 40 g. water. The initiators were added at a uniform rate over a period of 5 hours.

As the initial monomer charge was converted to polymer, the internal temperature was raised to 62° C. and held for 10 minutes. After seed conversion and a 10 minute hold at 62° C., polymerization was continued and a pre-emulsified blend of 325 g. vinyl acetate, 120 g. butyl acrylate, 14.8 g. hydroxypropyl acrylate and 29.6 g. 2-dimethoxymethyl phenoxy ethyl acrylate in a solution of 12 g. dodecyl benzene sulfonate, 12.68 g. Triton X305 (an alkyl aryl polyethylene oxide with 30 moles ethylene oxide), and 0.6 g. sodium acetate in 90 g. water was prepared.

The pre-emulsified monomer blend was added at a uniform rate over a period of 4 hours. The internal temperature was maintained at 62° C. until the polymerization was finished. At the end of the slow additions, 0.5 g. t-butyl hydroperoxide in 20 g. water was added uniformly over 5 minutes and the mixture was held for 20 g. methyl methacrylate were substituted for the vinyl acetate and butyl acrylate in the initial charge and 270 g. ethyl acrylate and 180 g. methyl methacrylate were used in the pre-emulsified monomer blend.

In the styrene/acrylic latex recipe, the initial charge contained 22.5 g. styrene and 27.5 g. butyl acrylate while the pre-emulsified monomer blend contained 202.5 g. styrene and 247.5 g. butyl acrylate.

In the control latex recipe, 31.5 g. N-methylol acrylamide (48% w/w solution in water) were used in the pre-emulsified monomer blend as a substitute for the acetal-containing monomer 2-(2-dimethoxymethylphenoxy)ethyl acrylate.

Several factors became evident from the results in Table II. First, the polymers obtained from blocked aldehyde (i.e., the acetal) monomers (DMPEA-2 and DMDPC) exhibited much better binder performance than those incorporating the unblocked (i.e., the aldehyde) monomers (EDFA and EDFC). Second, the acetal-containing binders show better solvent resistance (MEK tensile) than the N-methylol acrylamide-containing binders.

The poor performance of the aldehyde-containing polymers is due to precrosslinking of the polymers from chain transfer to the aldehyde. This was confirmed from both the intrinsic viscosity (IV) and % insoluble on the as-is sample of the binder. Polymers from the acetal-containing monomer (DMDPC) had an intrinsic viscosity in dimethyl formamide and % insoluble in methylethyl ketone of 1.5 and 0, respectively, whereas polymers from the aldehyde-containing monomers (EDFA and EDFC) had an intrinsic viscosity and % insolubles of 1 and 38, respectively.

EXAMPLE X

This example describes the method which would be used to prepare a pressure sensitive adhesive exhibiting permanent tackiness. The Tg of the interpolymer should range from +5° to −60° C.

A 1 l. reactor fitted with a mechanical stirrer, thermometer, addition funnels, and a reflux condenser is charged with 23.4 g. of a monomer mixture consisting of 160 g. 2-ethylhexyl acrylate, 40 g. of methyl acrylate, 20 g. of 2-(2-dimethoxymethylphenoxy)ethyl acrylate (DMPEA-2), 9 g. 2-hydroxyethyl acrylate and 5 g. of acrylic acid. The reactor is also charged with 75 g. of a 1:1 mixture of ethyl acetate and hexane along with 0.25 g. of azobisisobutyronitrile. The reaction mixture is heated to reflux and held for 15 min. at reflux (72° C.). The remainder of the monomer mixture and a solution of 2.5 g. azobisisobutyronitrile in 25 ml. ethyl acetate are added simultaneously via separate addition funnels over 2 hours. After the addition is complete, the solution is held at reflux until 99% of the monomers are converted to polymer. The solution is then cooled to 45° C. and enough ethyl acetate is added to bring the solids to 45%. The polymer should have a Mw of $2.5 \times 10^5$ and the Mn of $3.0 \times 10^4$.

A 100 g. solution of this polymer is mixed with 2 ml. of a 0.1% ammonium chloride solution in 90% alcohol, applied to a release paper, and heated to 100° C. for 3 minutes. It should give a highly tacky film.

EXAMPLE XI

The following example describes the preparation of a polymer dispersion of ethylene, vinyl acetate, and the acetal monomer. The emulsion should be useful as a non-woven binder for pulp, polyester, or rayon substrates.

A 10 l. stainless steel autoclave reaction vessel equipped with heating/cooling means, variable rate stirrer and means of metering monomers and initiators was employed. The reactor was charged with 600 g. Triton X301 (a sodium alkyl aryl polyethylene oxide sulfate with 3 moles ethylene oxide) as a 20% w/w water solution, 65 g. Triton X305 (an alkyl aryl polyethylene oxide with 30 moles ethylene oxide) as a 70% w/w water solution, 35 g. of sodium vinyl sulfonate as a 25% w/w water solution, 5.0 g. of a 1% water solution of ferrous sulfate, and 0.5 g. sodium acetate and 2.0 g. sodium metabisulfite in 1500 g. water. After purging with nitrogen 4000 g. of vinyl acetate were added. The reactor was pressurized to 450 psi with ethylene and equilibrated at 40° C. for 15 minutes. The polymerization was initiated by simultaneously metering in a solution of 14 g. of tertiary butyl hydroperoxide in 250 g. water and a solution of 28 g. sodium metabisulfite in 300 g. water. The initiators were added at a uniform rate over a period of 4.5 hours. After initiation occurred (as shown by a 2° C. increase in temperature), a mixture of 311 g. hydroxypropyl acrylate, 0.5 g. sodium acetate in 1000 g. water, and 631 g. of 2-(2-dimethoxymethylphenoxy)ethyl acrylate were separately and simultaneously added at a uniform rate over a period of 3 hours. At this point the temperature was increased to 65° C. and was maintained at 65° C. until the polymerization was finished. At the end of the slow additions, the reactor contents were transferred to a holding tank and degassed of excess ethylene. To the holding tank were charged 4.0 g. tertiary butyl hydroperoxide and 0.45 g. ammonium hydroxide in 40 g. water. After 15 minutes 4 g. of sodium metabisulfite and 0.45 g. ammonium hydroxide in 40 g. water were also added. After the additions the reaction mixture was cooled to 25°-30° C. and discharged.

Now that the preferred embodiments of the invention have been in detail, various modifications and improvements thereon will become readily apparent to those skilled in the art. Accordingly, the spirit and scope of the present invention are to be limited only by the appended claims, and not by the foregoing specification.

| | Tensile Results on Pulp Substrate | | | | | | | |
|---|---|---|---|---|---|---|---|---|
| Vinyl Acrylics Tested | % Pick Up (%) | Avg. Basis Weight (g/sq. yd) | Dry Peak Load (lb.) | Dry Peak Elong (%) | Wet Peak Load (lb.) | Wet Peak Elong (%) | MEK Peak Load (lb.) | MEK Peak Elong (%) |
| 75VA/25BA/3HPA/5.9DMPEA-2 | 12.6 | 37.6 | 5.95 | 4.7 | 1.64 | 11.1 | 1.77 | 3.6 |
| 75VA/25BA/3.9HPA/4.6EDFA* | 11.1 | 37.7 | 3.78 | 7.35 | 0.35 | 6.94 | 0.22 | 2.27 |
| 75VA/25BA/3.9HPA/5.0EDFC | 11.2 | 37.9 | 3.93 | 7.11 | 0.29 | 6.93 | 0.27 | 2.58 |
| 75VA/25BA/3.9HPA/6.4DMDPC | 11.0 | 37.3 | 5.24 | 6.44 | 1.42 | 10.53 | 1.50 | 4.20 |
| 75VA/25BA/3NMA (comparative) | 12.2 | 37.9 | 5.56 | 9.00 | 2.19 | 13.70 | 1.00 | 4.85 |

Comparative
*This polymer contained the aldehyde-containing monomer of U.S. Pat. No. 4,250,070.
DMPEA-2 is 2-(2-dimethoxymethylphenoxy)ethyl acrylate
DMDPC is (3,3-dimethoxy-2,2-dimethyl)propyl crotonate
VA is vinyl acetate
BA is butyl acrylate
HPA is hydroxypropy acrylate
EDFC is ethyl (2,2-dimethyl-2-formyl) crotonate
EDFA is ethyl(2,2-dimethyl-2-formyl) acrylate
NMA is N-methylolacrylamide

TABLE III

| | Tensile Evaluation Of All Acrylic Latices With 2-DMPEA | | | | | | | |
|---|---|---|---|---|---|---|---|---|
| Acrylics Tested | Pick Up (%) | Basis Weight (gsy) | Dry Peak Load (lbs.) | Dry Peak Elong (5) | Wet Peak Load (lb.) | Wet Peak Elong (%) | MEK Peak Load (lb.) | MEK Peak Elong (%) |
| Tensile Results on Pulp Substrate | | | | | | | | |
| 95EA/5MMA/1MAA/2.5NMA (Comparative) | 11.3 | 38.2 | 3.71 | 7.8 | 2.11 | 13.7 | 1.33 | 4.5 |
| 95EA/5MMA/3HEA/6DMPEA-2 | 11.1 | 37.5 | 3.81 | 5.1 | 1.47 | 10.7 | 2.14 | 4.6 |
| 56BA/44MMA/3NMA (Comparative) | 11.7 | 38.6 | 5.14 | 6.8 | 2.39 | 11.9 | 1.21 | 3.9 |
| 56BA/44MMA/3HEA/6DMPEA-2 | 12.7 | 38.6 | 5.43 | 6.1 | 1.78 | 10.6 | 2.22 | 4.4 |
| Tensile Results On Polyester Substrate | | | | | | | | |

TABLE III-continued

| | | Dry | Dry | Wet | Wet | MEK | MEK |
| Acrylics Tested | Pick Up (%) | Basis Weight (gsy) | Peak Load (lbs.) | Peak Elong (5) | Peak Load (lb.) | Peak Elong (%) | Peak Load (lb.) | Peak Elong (%) |
| --- | --- | --- | --- | --- | --- | --- | --- | --- |
| 95EA/5MMA/3HEA/6DMPEA-2 | 41.9 | 24.7 | 0.71 | 50.2 | 0.32 | 27.8 | 0.04 | 10.1 |
| 95EA/5MMA/1MAA/2.5NMA (Comparative) | 42.3 | 18.6 | 1.27 | 35.8 | 0.79 | 23.1 | 0.34 | 7.6 |
| 56BA/44MMA/3HEA/6DMPEA-2 | 42.3 | 17.3 | 1.11 | 32.8 | 0.78 | 18.6 | 0.04 | 8.8 |
| 56BA/44MMA/3NMA (Comparative) | 40.9 | 19.4 | 1.69 | 30.1 | 1.38 | 25.9 | 0.26 | 5.9 |

Tensile Evaluation Of All Acrylic Latices With 2-DMPEA

EA is ethyl acrylate
MMA is methyl methacrylate
HEA is hydroxyethyl acrylate
DMPEA is (2,2-dimethoxymethylphenoxy)ethyl acrylate
NMA is N-methylolacrylamide

What is claimed is:

1. An acetal-containing monomer selected from the group consisting of (3,3-dimethoxy-2,2-dimethyl)propyl crotonate, (3,3-dimethoxy-2,2-dimethyl)propyl fumarate, (3,3-dimethoxy-2,2-dimethyl)propyl maleate, (3,3-dimethoxy-2,2-dimethyl)propyl itaconate, bis(3,3-dimethoxy-2,2-dimethyl)propyl fumarate, bis(3,3-dimethoxy-2,2-dimethyl)propyl maleate, and bis(3,3-dimethoxy-2,2-dimethyl) propyl itaconate.

2. A polymer comprising an ethylenically unsaturated monomer and an acetal-containing monomer selected from the group consisting of (3,3-dimethoxy-2,2-dimethyl)propyl crotonate; (3,3-dimethoxy-2,2-dimethyl)propyl fumarate; (3,3-dimethoxy-2,2-dimethyl)propyl maleate; (3,3-dimethoxy-2,2-dimethyl)propyl itaconate; bis-(3,3-dimethoxy-2,2-dimethyl)propyl fumarate; bis(3,3-dimethoxy-2,2-dimethyl)propyl maleate; bis(3,3-dimethoxy-2,2-dimethyl)propyl itaconate; [5-(dimethoxymethyl)furfur-2-yl]methyl acrylate; 5-(N,N-di[propyl-1-en-3]amino-methyl)-2-dimethoxymethyl furan; 2-(dimethoxymethylphenoxy)ethyl acrylate; 2-(2-[2-(1,3-dioxolano)]phenoxy)ethyl acrylate; 2-hydroxy-3-(4-dimethoxymethylphenoxy)propyl methacrylate; and 2-hydroxy-3-(2-dimethoxymethyl phenoxy)propyl methacrylate.

3. A monomer containing aromatic acetal groups selected from the group consisting of [5-(dimethoxymethyl)furfur-2-yl]methyl acrylate, 5-(N,N-di-[n-propyl-1-en-3-yl]aminomethyl)-2-dimethoxymethyl furan, 5-(n-propyl-1-en-3-oxymethyl)-2-dimethoxymethyl furan, and 5-(n-propyl-1-en-3-aminomethyl)-2-dimethoxymethyl furan.

4. A monomer containing aromatic acetal groups which is selected from the group consisting of 2-(2-dimethoxymethyl-phenoxy)ethyl acrylate, 2-(2-(2-(1,3-dioxalano)phenoxy)ethyl acrylate, 2-hydroxy-3-(4-dimethoxymethylphenoxy)propyl methacrylate, and 2-hydroxyl-3-(2-dimethoxymethyl-phenoxy)propyl methacrylate.

5. The polymer of claim 2, wherein the alkyl acrylate is ethyl acrylate or butyl acrylate; wherein the alkyl methacrylate is methyl methacrylate; wherein the hydroxyalkyl acrylate is 2-hydroxyethyl acrylate or 2-hydroxypropyl acrylate; wherein the vinyl ester is vinyl acetate; wherein the acetal-containing monomer is selected from the group consisting of [5-(dimethoxymethyl)furfur-2-yl]methyl acrylate, [5-(dimethoxymethyl)-furfur-2-yl]methyl methacrylate, 5-(N,N-di-[propyl-1-en-3-]aminoethyl)-2-dimethoxymethyl furan, (3,3-dimethoxy-2,2-dimethyl)propyl crotonate, (3,3-dimethoxy-2,2-dimethyl)propyl maleate, bis(3,3-dimethoxy-2,2-dimethyl)propyl itaconate, bis(3,3-dimethoxy-2,2-dimethyl)propyl fumarate, bis(3,3-dimethoxy-2,2-dimethyl) propyl maleate, 2-(2-dimethoxymethylphenoxy)ethyl acrylate, 2-hydroxy-3-(4-dimethoxymethylphenoxy)propyl methacrylate, 2-hydroxy-3-(2- dimethoxymethylphenoxy)propyl methacrylate, bis(3,3-dimethoxy-2,2-dimethyl)propyl crotonate, and (3,3,-dimethoxy-2,2,-dimethyl)propyl itaconate.

6. The polymer of claim 2, wherein the ethylenically unsaturated monomers are a hydroxyalkyl acrylate or methacrylate and an alkyl acrylate or methacrylate; or wherein the ethylenically unsaturated monomers are a hydroxyalkyl acrylate or methacrylate, ethylene, and a vinyl ester; or wherein the ethylenically unsaturated monomers are a hydroxyalkyl acrylate or methacrylate and styrene and/or acrylonitrile and an alkyl acrylate of methacrylate.

7. An aqueous emulsion, adapted for producing nonwovens, containing the polymer of claim 5.

8. The monomer of claim 3, wherein the monomer is [5-(dimethoxymethyl)furfur-2-yl]methyl acrylate.

9. The monomer of claim 3, wherein the monomer is 5-(N,N-di-[n-propyl-1-en-3-yl]aminomethyl)-2-dimethoxymethyl furan.

10. The monomer of claim 4, wherein the monomer is 2-(2-dimethoxymethylphenoxy)ethyl acrylate.

* * * * *

UNITED STATES PATENT AND TRADEMARK OFFICE
CERTIFICATE OF CORRECTION

PATENT NO. : 5,258,477
DATED : November 2, 1993
INVENTOR(S) : Robert L. Billmers et al It is certified that error appears in the above-indentified patent and that said Letters Patent is hereby corrected as shown below:

On the title page Item (19), "Tsai et al" should read
-- Billmers et al --.

On the title page, Inventors should read

--(75) Inventors: Robert L. Billmers, Stockton;
Rama S. Chandran, South Bound Brook; Paul R. Mudge,
Belle Mead; Michael T. Sarkis, Lawrenceville, all of
N.J.--.

Signed and Sealed this

Second Day of August, 1994

Attest:

BRUCE LEHMAN

Attesting Officer        Commissioner of Patents and Trademarks